United States Patent [19]
Yamaguchi et al.

[11] Patent Number: 5,460,832
[45] Date of Patent: Oct. 24, 1995

[54] SKIN COSMETIC HAVING AN EGG WHITE ENZYME HYDROLYSATE WITH HYALURONIC ACID SYNTHESIS PROMOTING ACTIVITY

[75] Inventors: Hiroaki Yamaguchi; Akio Kawasaki; Masatsugu Yamashita, all of Yokkaichi, Japan

[73] Assignee: Taiyo Kagaku Co., Ltd., Yokkaichi, Japan

[21] Appl. No.: 10,877

[22] Filed: Jan. 29, 1993

[30]  Foreign Application Priority Data

Jan. 31, 1992 [JP] Japan .................................. 4-046322
May 12, 1992 [JP] Japan .................................. 4-192650

[51] Int. Cl.⁶ ......................... A61K 31/715; A61K 37/00
[52] U.S. Cl. ................................. 424/581; 514/2
[58] Field of Search .................... 514/62, 54, 2; 424/581

[56] References Cited

U.S. PATENT DOCUMENTS 5,153,174  10/1992  Band et al. ............................ 514/12

FOREIGN PATENT DOCUMENTS 15851    6/1975  Japan .
3190808  8/1991  Japan .

*Primary Examiner*—Raymond Henley, III
*Assistant Examiner*—Phyllis G. Spivack
*Attorney, Agent, or Firm*—Birch, Stewart, Kolasch & Birch

[57] ABSTRACT

The invention is directed to a skin cosmetic comprising an egg white enzyme hydrolysate and/or a fractional component thereof which possesses hyaluronic acid synthesis promoting activity.

9 Claims, No Drawings

SKIN COSMETIC HAVING AN EGG WHITE ENZYME HYDROLYSATE WITH HYALURONIC ACID SYNTHESIS PROMOTING ACTIVITY

FIELD OF THE INVENTION

The present invention relates to a skin cosmetic containing a substance possessing hyaluronic acid synthesis promoting activity, and more specifically to a skin cosmetic containing an egg white enzyme hydrolysate possessing hyaluronic acid synthesis promoting activity or a fractional component thereof.

BACKGROUND OF THE INVENTION

In Japan, a medical interest in aging is increasing as an aging society is being approached. Accordingly, the mechanism of skin aging and other subjects in the field of dermatology are under investigation, and the control of aging by cell potentiator administration is drawing much attention both in Japan and abroad.

Traditionally, some animal, plant or fungal extracts have been used in pharmaceuticals and cosmetics, with the recognition of the tissue potentiating activity thereof. However, few of them have been assessed as exhibiting bioactivity at cell level. For example, attempts have been made to determine the increase in oxygen consumption caused by the addition of these extracts to tissue sections using Warburg's manometer, etc., or to determine the tissue potentiating activity using an enzyme which catalyzes oxidative phosphorylation for ATP, etc. However, in these means, for example, the oxygen consumption determination method using tissue sections shows that water as well possesses potentiating activity; even it can be said that many substances containing a carbon or nitrogen source, at appropriate concentrations, increase oxygen consumption. Although these means are effective at least in the evaluation of tissue potentiators as nutritive agents, there have been many difficulties in assessing cell potentiating activity by these means, provided that samples are evaluated from the viewpoint of skin function at cell level.

Histochemically, the skin can be roughly divided into the epidermis, the dermis and the subcutaneous tissue. Particularly the dermis, as a skin supporting tissue, plays a key role in the maintenance of skin homeostasis. The dermis is configured mainly with fibroblasts, which produce proteins such as collagen and glycosaminoglycans such as hyaluronic acid to form a constructive structure in these connective tissues.

The major glycosaminoglycan present in the skin dermal tissue is hyaluronic acid, a high molecular compound of a molecular weight of up to several millions having repeat units comprising glucuronic acid and N-acetylglucosamine bound via β-glycoside bond. Hyaluronic acid is also abundantly contained in chicken crests, umbilical cords, ocular glass and secretions such as joint fluid. Also, since hyaluronic acid has a very long acidic sugar chain, it is expected to have the action as a kind of polyanion, with high water retention capability; 1 g of hyaluronic acid can retain as much of 6 liters of water. Physiologically, it can therefore be conjectured that skin flexibility may be closely associated with the function of this substance.

In recent years, various studies of aging have been conducted, and hyaluronic acid has proven to play a key role in skin function. Various cosmetics have been formulated with hyaluronic acid derived from chicken crest or Streptococcal microbial fermentation to utilize the excellent functions of hyaluronic acid, such as skin moisture retention. However, these cosmetics remain on the skin surface and merely exhibit moisture retaining action attributable to the water absorbing property thereof, since they offer nothing more than skin surface application of hyaluronic acid and since the absorption of hyaluronic acid, as a high molecular substance, is hampered by the epidermal barrier. The effect disappears upon washing down the cosmetic; such conventional cosmetics do not offer essential improvement in skin function.

Hyaluronic acid, playing a key role in skin function, has been reported to decrease with aging. Miyamoto et al. investigated the relationship among hyaluronic acid, skin moisture content and aging, using the rat skin, and found that hyaluronic acid had very high values in the fetal and neonatal stages and decreased rapidly until 4 weeks of age, followed by gradual decrease. It was also shown that the hyaluronic acid decreasing pattern and the dry yield pattern are in a reverse correlation, accordingly the dermal water content depends strongly on hyaluronic acid (J. Soc. Cosmet. Chem. Japan, 15, 77, 1981).

In a study using fibroblasts derived from human fetal lung, Matsuoka et al. showed that glycosaminoglycan synthesis decreases with the number of subculture generations, and that hyaluronic acid decreases markedly (Cell Structure and Function, 9, 357, 1984).

Also, Maria et al. determined hyaluronic acid contents in normal human female skin and demonstrated a reduction in skin hyaluronic acid content with aging (Carbohydrate Research, 159, 127-136, 1987).

From these findings, it is evident that hyaluronic acid synthesis in skin fibroblasts decreases with aging. This suggests a potential for suppression of morphological changes in aged skin, such as wrinkles, by increasing the dermal hyaluronic acid content and hence providing flexibility and smoothness for the skin, provided that hyaluronic acid synthesis can be promoted.

SUMMARY OF THE INVENTION

An object of the present invention is to provide a novel skin cosmetic which possesses aging-controlling function by promoting hyaluronic acid synthesis in dermal fibroblasts.

To assess samples at cell level, the present inventors have first tested the hyaluronic acid synthesizing capability of cultured fibroblasts in accordance with the method of Matsuoka (Mech. Dev., 15, 153–163, 1981) and Otsuka et al. (Biochim, Biophys. Acta., 444, 359–368, 1976). Specifically, this testing method comprises adding the sample to a cell culture system, followed by allowing the cells to incorporate tritium-labeled glucosamine hydrochloride to quantify hyaluronic acid in the culture supernatant.

The present inventors have screened various substances, selected optionally from animal, plant and fungal species, for hyaluronic acid synthesis promoting action, by the above testing method, and detected high hyaluronic acid synthesis promoting activity in egg white enzyme hydrolysate or a fractional component thereof.

Further, the present inventors prepared a skin cosmetic formulated with an egg white enzyme hydrolysate possessing hyaluronic acid synthesis promoting activity or a fractional component thereof and applied it to skin, and found that skin function is accentuated so that the skin becomes smooth and well-moistened, and confirmed that this skin cosmetic is very safe. The inventors made further investigations based on this finding, and developed the present invention. -The skin cosmetic of the present invention, formulated with an egg white enzyme hydrolysate possessing hyaluronic acid synthesis promoting activity or a fractional component thereof, seems to exhibit its effect by promoting hyaluronic acid synthesis in dermal fibroblasts.

Since ancient times, chicken eggs have long been used as an important food. Moreover, chicken eggs are used widely in various cuisines or in the entire food industry with utilizing the thermal solidifying property of egg yolk and egg white, the whippability of egg white, the emulsifiability of egg yolk and other properties. Also, egg white hydrolysates have recently been used as moisture retaining and skin protecting components in skin cosmetics, shampoos and rinsing agents.

However, there has been no investigation of the hyaluronic acid synthesis promoting action of egg white enzyme hydrolysate or a fractional component thereof or its utility attributable to this action when it is formulated in skin cosmetics. This is quite the first achievement by the present inventors.

Specifically, the present invention provides a novel skin cosmetic containing an egg white enzyme hydrolysate possessing hyaluronic acid synthesis promoting activity and/or a fractional component thereof.

DETAILED DESCRIPTION OF THE INVENTION

The present invention is hereinafter described more in detail.

The above-described test for hyaluronic acid synthesis promoting activity, used in the course to the present invention, is not limitative in the test of the hyaluronic acid synthesis promoting activity. Other testing methods capable of detecting hyaluronic acid synthesizing capability at cell level can be used in vitro and in vivo, including the method wherein glycosaminoglycans in the culture supernatant are sequentially lysed enzymatically, and the resulting unsaturated disaccharides are analyzed by HPLC, and the method wherein hyaluronic acid in the culture supernatant is quantified by enzyme immunoassay.

In carrying out the present invention, chicken egg white is first decomposed enzymatically. In addition to fresh egg white, frozen egg white, aqueous solutions of powdered egg white, and egg white preparations obtained by removing mucin, lysozyme, etc. from egg white can also be used, with a preference given to aqueous solutions of powdered egg white.

Any protease as an enzyme can be used for the present invention, as long as it is capable of producing an egg white enzyme hydrolysate possessing hyaluronic acid synthesis promoting activity from egg white. Examples of such proteases include thiol proteases such as papain, cathepsin $B_1$, ficin, bromelain, chymopapain, *Clostridium histolyticum* proteinase and Streptococcal proteinase, serine proteases such as trypsin, plasmin, *E. coli* protease II, elastase and proteinase K, and other endopeptidases. These peptidases are optionally used, with a preference given to trypsin, papain and cathepsin $B_1$.

Since optimum pH varies among proteases, it is preferable to previously adjust the egg white solution to the optimum pH for the protease to be used before enzyme treatment. When trypsin is used, pH is adjusted to 6 to 9. In the case of papain, it is pH of 6 to 9, and in the case of cathepsin B1, it is pH of 5 to 8. Although the amount of protease added varies depending on the kind of enzyme used, it is normally 0.01 to 5% by weight, preferably 0.1 to 1% by weight relative to the egg white solution. Also, it is effective to carry out the enzyme treatment while stirring the starting materials in a tank equipped with a temperature controller using a stirrer, etc.

Although the reaction may be carried out at room temperature or high temperature of 40° to 80 ° C., it is preferable to maintain a reaction temperature in the range from 50° to 70° C. The duration of enzyme treatment varies depending on the kind and amount of the protease used. When papain is used, an enzyme treatment is carried out for 10 to 48 hours and then the enzymes in the egg white solution are inactivated by retaining the egg white solution at 85° to 100° C. for a given period. When trypsin is used, an enzyme treatment is carried out for 20 to 48 hours, followed by an enzyme inactivation at 85° to 100 ° C. When cathepsin $B_1$ is used, an enzyme treatment is carried out for 10 to 40 hours, followed by an enzyme inactivation at 85° to 100 ° C.

The insoluble substance resulting from such an enzyme treatment is removed by filtration, centrifugation, decantation or other means to obtain an egg white enzyme hydrolysate rich in the desired hyaluronic acid synthesis promoting component. This egg white enzyme hydrolysate may be adjusted to an appropriate pH as necessary and subjected to gel filtration or ultrafiltration to remove the high molecular substances (molecular weight: not less than 10000) without inactivation of the hyaluronic acid synthesis promoting activity, and may be fractionated using anion or cation exchange resin to purify the desired component by any of the column method and the batch method. In this case, a fraction of molecular weight of 100 to 10000, preferably 100 to 4000 is used from the viewpoint of allergenicity. Also, this egg white enzyme hydrolysate or a fractional component thereof may be concentrated by concentration under reduced pressure, ultrafiltration, freeze dry concentration and other methods, and may also be prepared as dry powder by freeze drying, spray drying, plate drying and other methods.

In a skin cosmetic of the present invention, either the egg white enzyme hydrolysate or a fractional component thereof, or both of them can be used as an effective component.

The content of the egg white enzyme hydrolysate and/or a fractional component thereof in a skin cosmetic of the present invention is normally 0.01 to 20% by weight, preferably 0.1 to 10% by weight. When the content exceeds 20% by weight, more effects are not obtained, and when the content is less than 0.01% by weight, the sufficient effects cannot be obtained.

In addition to the above essential components, the skin cosmetic of the present invention may be formulated as necessary with additives used commonly in cosmetics, such as surfactants, oils and fats, polyhydric alcohols, lower alcohols, thickening agents, UV absorbents, light scattering agents, preservatives, antioxidants, chelating agents, pH regulators, flavoring agents, pigments and water. Specifically, these additives are exemplified as follows:

Examples of surfactants include polyoxyethylene (hereinafter abbreviated as POE-) branched alkyl ethers such as POE-octyldodecyl alcohol and POE-2-decyltetradecyl alcohol, POE-alkyl ethers such as POE-oleyl alcohol ether and POE-cetyl alcohol ether, sorbitan esters such as sorbitan monooleate, sorbitan monoisostearate and sorbitan monolaurate, POE-sorbitan esters such as POE-sorbitan monooleate, POE-sorbitan monoisostearate and POE-sorbitan monolaurate, fatty acid esters of glycerol such as glyceryl monooleate, glyceryl monostearate and glyceryl monomyristate, POE-fatty acid esters of glycerol such as POE-glyceryl monooleate, POE-glyceryl monostearate and POE-glyceryl monomyristate, POE-dihydrocholesterol ester, POE-hardened castor oil, POE-hardened castor oil fatty acid esters such as POE-hardened castor oil isostearate, POE-alkylaryl ethers such as POE-octylphenol ether, glycerol esters such as glycerol monoisostearate and glycerol monomyristate, POE-glycerol ethers such as POE-glycerol monoisostearate and POE-glycerol monomyristate, polyglycerol fatty acid esters such as diglyceryl monostearate, decaglyceryl decastearate, decaglyceryl decaisostearate and diglyceryl diisostearate and other nonionic surfactants; potassium salts, sodium salts, diethanolamine salts, triethanolamine salts, amino acid salts and other salts of higher fatty acids such as myristic acid, stearic acid, palmitic acid, behenic acid, isostearic acid and oleic acid, the above alkali salts of ether carboxylic acids, salts of N-acylamino acids, N-acylsalconates, higher alkylsulfonates and other anionic surfactants; alkylamine salts, polyamine, aminoalcohol fatty acids, organic silicone resin, alkyl quaternary ammonium salts and other cationic surfactants; and lecithin, betaine derivatives and other amphoteric surfactants.

Examples of oils and fats include vegetable oils and fats such as castor-oil, olive oil, cacao oil, camellia oil, coconut oil, wood wax, jojoba oil, grape seed oil and avocado oil; animal oils and fats such as mink oil and egg yolk oil; waxes such as beeswax, whale wax, lanolin, carnauba wax and candelilla wax; hydrocarbons such as liquid paraffin, squalene, microcrystalline wax, ceresine wax, paraffin wax and vaseline; natural or synthetic fatty acids such as lauric acid, myristic acid, stearic acid, oleic acid, isostearic acid and behenic acid; natural or higher alcohols such as cetanol, stearyl alcohol, hexyldecanol, octyldecanol and lauryl alcohol; and esters such as isopropyl myristate, isopropyl palmitate, octyldodecyl myristate, octyldodecyl oleate and cholesterol oleate.

Examples of polyhydric alcohols include ethylene glycol, polyethylene glycol, propylene glycol, 1,3-butyrene glycol, 1,4-butyrene glycol, dipropylene glycol, glycerol, diglycerol, triglycerol, tetraglycerol and other polyglycerols, glucose, maltose, maltitose, sucrose, fructose, xylitose, sorbitol, maltotriose, threitol and erythritol.

Examples of thickening agents include naturally-occurring high molecular substances such as sodium alginate, xanthene gum, aluminum silicate, quince seed extract, gum tragacanth, starch, collagen and sodium hyaluronate; semi-synthetic high molecular substances such as methyl cellulose, hydroxyethyl cellulose, carboxymethyl cellulose, soluble starch and cationized cellulose; and synthetic high molecular substances such as carboxyvinyl polymer and polyvinyl alcohol.

Examples of UV absorbents include p-aminobenzoic acid, 2-ethoxyethyl p-methoxycinnamate, isopropyl p-methoxycinnamate, butylmethoxybenzoylmethane, glyceryl-mono-2-ethylhexanoyl-di-p-methoxybenzophenone, digalloyl trioleate, 2,2'-dihydroxy-4-methoxybenzophenone, ethyl-4-bishydroxypropylaminobenzoate, 2-ethylhexyl-2-cyano-3, 3'-diphenyl acrylate, ethylhexyl p-methoxycinnamate, 2-ethylhexyl salicylate, glyceryl p-aminobenzoate, homomethyl salicylate, methyl o-aminobenzoate, 2-hydroxy-4-methoxybenzophenone, amyl p-dimethylaminobenzoate, 2-phenylbenzoimidazole-5-sulfonic acid and 2-hydroxy-4-methoxybenzophenone-5-sulfonic acid.

Examples of preservatives include benzoates, salicylates, sorbates, dehydroacetates, p-oxybenzoates, 2,4,4'-trichloro-2'-hydroxydiphenyl ether, 3,4,4'-trichlorocarbanilide, benzalkonium chloride, hinokitiol, resorcinol and ethanol.

Examples of antioxidants include tocopherol, ascorbic acid, butylhydroxyanisole, dibutylhydroxytoluene, nordihydroguaiaretic acid and propyl gallate.

Examples of chelating agents include sodium edetate and sodium citrate.

Some of these additives function to enhance the efficacy of the skin cosmetic of the present invention by increasing the stability or percutaneous absorbability of the essential components of the present invention.

Also, any dosage form is acceptable, whether in solution, emulsion, powder dispersion, or others. Applicability is wide, including fundamental cosmetics such as lotions, emulsions, creams and packs, and make-up cosmetics such as foundation.

As stated above, a skin cosmetics containing a substance possessing hyaluronic acid synthesis promoting activity, i.e., an egg white enzyme hydrolysate or a fractional component thereof promote the skin function and possess the aging-controlling function which protects skin from the wrinkles and makes skin smooth and well-moistened. Also, as they are highly safe, the applications to the clinical fields are desired.

EXAMPLES

The results of a test for the efficacy and safety of the thus-obtained skin cosmetic of the present invention are as follows:

Test Example 1. Hyaluronic acid synthesizing activity of cultured fibroblasts

After sample addition, subcultured 3T6 Swiss Albino cells (mouse embryonic cells) were cultured on Dulbecco's modified MEM medium (containing 0.5% fetal bovine serum) under low serum culturing conditions at 37° C. in 5% $CO_2$+95% air for 4 days. Then 200 μl of $^3$H-glucosamine hydrochloride (250 μCi/ml) was added, followed by 48 hours of cultivation at 37° C. in 5% $CO_2$+ air. For a control, the same experiment was conducted except that no sample was added. The culture supernatant was recovered from each petri dish and subjected to an alkali treatment, an Actinase (manufactured by Kaken Kagaku Co.) treatment, and deproteinization with trichloroacetic acid, after which hyaluronic acid was specifically decomposed with hyaluronidase (manufactured by Seikagaku Kogyo Co.), and the unlysed glycosaminoglycan was removed by the cetyl pyridinium chloride precipitation method, the lysate was mixed with HIONIC FLUOR (manufactured by Packard Instrument Co.) and radioactivity was counted. The results are shown in Table 1. The method for sample preparation and the amount of its addition to the medium are described below.

Sample A: Egg white enzyme hydrolysate possessing hyaluronic acid synthesis promoting activity 5 g of dry powder of chicken egg white was dissolved in 95 g of water. After this solution was adjusted to a pH of 8.0, 0.5 g of trypsin was added, followed by 48 hours of reaction at 40° C. Next, the heating treatment was performed at 90° C., and then the resulting insoluble substance was removed by aspiration filtration.

Sample B: Fractional component of egg white enzyme lysate possessing hyaluronic acid synthesis promoting activity 5 g of dry powder of chicken egg white was dissolved in 100 g of water. .After this solution was adjusted to a pH of 8.0, 0.5 g of trypsin was added, followed by 48 hours of reaction at 40° C. The resulting insoluble substance was removed by aspiration filtration. The solution was adsorbed to DEAE Cellulofine (manufactured by Seikagaku Kogyo Co.), equilibrated with 0.01M phosphate buffer, pH 8.5, and then eluted with 0.8M NaCl and 0.01M phosphate buffer, pH 8.5. The eluate was freeze-dried to yield dry powder, which was dissolved in water to yield a 10% aqueous solution.

Sample C: Fractional component of egg white enzyme lysate possessing hyaluronic acid synthesis promoting activity 5 g of dry powder of chicken egg white was dissolved in 95 g of water. After this solution was adjusted to a pH of 7.5, 0.6 g of papain was added, followed by 48 hours of reaction at 50° C. After a heat treatment at 90° C., the resulting insoluble substance was removed by aspiration filtration. The solution was dialyzed at 4° C. for 15 hours and then adsorbed to DEAE Cellulofine (manufactured by Seikagaku Kogyo Co.), equilibrated with 0.01M acetate buffer, pH 7.5, and then eluted with 1M NaCl and 0.01M acetate buffer, pH 7.5. The eluate was spray-dried to yield dry powder, which was dissolved in water to yield a 10% aqueous solution.

Sample D: Fractional component of egg white enzyme lysate possessing hyaluronic acid synthesis promoting activity 5 g of dry powder of chicken egg white was dissolved in 95 g of water. After addition of 0.1 g of cysteine hydrochloride, this solution was adjusted to a pH of 6.5, and 0.4 g of cathepsin $B_1$ was added, followed by 24 hours of reaction at 60° C. After a heat treatment at 90° C., 1 g of "Carboraffin" (manufactured by Takeda Chemical Industries, Ltd.) was added, followed by vigorous stirring and subsequent aspiration filtration, to yield a clear filtrate. This filtrate was dried on a plate to yield dry powder, which was dissolved in water to yield a 10% aqueous solution.

Sample E: Fractional component of egg white enzyme lysate possessing hyaluronic acid synthesis promoting activity The DEAE Cellulofine eluate obtained from sample B was dialyzed at 4° C. for 12 hours. After high molecular fraction removal through an ultrafiltration membrane (manufactured by Millipore Co.; fractional molecular weight of 10000), the dialysate was spray-dried to yield dry powder, which was dissolved in water to yield a 10% aqueous solution.

Sample F: Fractional component of egg white enzyme lysate possessing hyaluronic acid synthesis promoting activity To the DEAE Cellulofine eluate obtained from sample C was added 2% particulate "Shirasagi Y" (manufactured by Takeda Chemical Industries, Ltd.). After vigorous stirring, aspiration filtration was conducted to yield a clear filtrate. After high molecular fraction removal through an ultrafiltration membrane (manufactured by Millipore Co.; fractional molecular weight of 10000), the filtrate was freeze-dried to yield dry powder, which was dissolved in water to yield a 10% aqueous solution.

Sample G: Fractional component of egg white enzyme lysate possessing hyaluronic acid synthesis promoting activity The filtrate obtained from sample D was further subjected to an ultrafiltration (Millipore Co.; fractional molecular weight of 10000) to remove high molecular substance therefrom. The filtrate thus obtained was freeze-dried to yield dry powder, which was dissolved in water to yield a 10% aqueous solution. t,0190 t,0200

As is clear from Table 1, the chicken egg white enzyme hydrolysate or a fractional component thereof promotes hyaluronic acid synthesis in fibroblasts.

Test Example 2. Panel test

A sensory evaluation test was conducted, in which 50 women suffering from wrinkles, aged 31 to 52 years (40.2 years on average), were requested to use the skin cosmetic of the present invention or a control skin cosmetic (their compositions are shown below) as applied twice (morning, evening) daily for three consecutive months. The results of the sensory evaluations are given in Table 2. t,0210 t,0211

As is clear from Table 2, the skin cosmetics of the present invention show the high efficacy.

Test Example 3. Patch test

A closed patch test was conducted, in which a total of 30 subjects (17 males, 13 females), aged 21 to 64 years, had sample B of Test Example 1 kept in contact with the skin in their brachial flexion area.

The evaluation criteria used are as follows:

−: no reaction,
±: slight erythema,
+: distinct erythema, and
++: erythema and swelling/eruption.

All subjects were judged as "−" (no reaction), demonstrating that the skin cosmetic of the present invention is very safe with little potential for induction of irritative or allergic reaction.

The present invention is hereinafter described in more detail by the following preparation examples of skin cosmetic, but the present invention is not limited by them.

Preparation Example 1: Lotion t,0230

Preparation Example 2: Cream t,0231

Preparation Example 3: Emulsions t,0240

Preparation Example 4: Packs t,0241

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A skin cosmetic comprising a fractional component having a molecular weight of 100 to 10,000 of an egg white enzyme hydrolysate, said fractional component of egg white enzyme hydrolysate possesses hyaluronic acid synthesis promoting activity.

2. The skin cosmetic according to claim 1, wherein the amount of said fractional component of egg white enzyme hydrolysate in said skin cosmetic is from 0.01 to 20% by weight.

3. The skin cosmetic according to claim 1, wherein said fractional component has a molecular weight of 100 to 4,000.

4. The skin cosmetic according to claim 1, wherein the amount of said fractional component of egg white enzyme hydrolysate in said skin cosmetic is from 0.1 to 10% by weight.

5. A skin cosmetic comprising 0.01 to 20% by weight of a fractional component having a molecular weight of 100 to 10,000 of an egg white enzyme hydrolysate, said fractional component possessing hyaluronic acid synthesis promoting activity.

6. The cosmetic composition of claim 5, in the form of a lotion.

7. The cosmetic composition of claim 5, in the form of a cream.

8. The cosmetic composition of claim 5, in the form of a emulsion.

9. A method of treating skin to promote synthesis of hyaluronic acid in the skin dermal tissues, comprising the step of applying to skins a skin cosmetic comprising an egg white enzyme hydrolysate and/or a fractional component thereof.

* * * * *